(12) United States Patent
Del Mar

(10) Patent No.: US 6,605,046 B1
(45) Date of Patent: Aug. 12, 2003

(54) AMBULATORY PHYSIO-KINETIC MONITOR WITH ENVELOPE ENCLOSURE

(75) Inventor: Bruce E. Del Mar, Laguna Beach, CA (US)

(73) Assignee: Del Mar Medical Systems, LLC, Irvine, CA (US)

(*) Notice: Subject to any disclaimer, the term of this patent is extended or adjusted under 35 U.S.C. 154(b) by 374 days.

(21) Appl. No.: 09/616,654

(22) Filed: Jul. 14, 2000

Related U.S. Application Data

(63) Continuation-in-part of application No. 09/325,321, filed on Jun. 3, 1991, now abandoned.

(51) Int. Cl.[7] .............................................. A61B 5/0402
(52) U.S. Cl. ....................... 600/507; 128/917; 600/386
(58) Field of Search ................................. 600/509, 513, 600/520, 521, 523, 386–393; 128/917–918

(56) References Cited

U.S. PATENT DOCUMENTS

| 5,027,824 | A | * | 7/1991 | Dougherty et al. | ......... | 600/509 |
| 5,263,491 | A | * | 11/1993 | Thornton | ..................... | 600/574 |
| 6,117,077 | A | * | 9/2000 | Del Mar et al. | ............ | 600/301 |

* cited by examiner

Primary Examiner—Jeffrey R. Jastrzab
(74) Attorney, Agent, or Firm—W.D. English, Esq.

(57) ABSTRACT

A water and moisture sealed, self contained, compact, long term, ambulatory physio-kinetic monitor is designed for mounting directly to the skin of an athlete or fitness performer, preferably immediately adjacent to the organ or system that is to be monitored, and is adhesively held there in place, covertly and comfortably, under clothing by disposable electrode, adhesive skin pads. At least three positive electrodes and a common negative electrode extend from the monitor and attach by similar disposable adhesive electrode pads to detect physiological, e.g. ECG data. Accelerometer means disposed within the monitor detects body movement and likewise stores that data on a third ECG data channel.

2 Claims, 14 Drawing Sheets

FIG. 8b

AMBULATORY PHYSIO-KINETIC MONITOR WITH ENVELOPE ENCLOSURE

This application is a Continuation in Part (CIP) of a U.S. patent application Ser. No. 09/325,321, filed Jun. 3, 1999 now abandoned.

BACKGROUND OF THE INVENTION

1. Field of the Invention

Generally speaking, the invention relates to apparatus and processes for long term, ambulatory monitoring and accumulation of human physiological data. More specifically, the invention disclosed herein consists of a miniature, solid state recorder for ambulatory monitoring of body signals, electrocardiographic data in particular, and related body motions over extended periods of time in general mobile activities and in particular in athletic activities, sealed against moisture and other contaminants by an encapsulating envelope or inverted pouch, mounted under clothing, and supported by conventional skin mounted electrode adhesive pads attaching the recorder or the encapsulating, sealing envelope directly to the patient's chest. The recorder and/or sealing envelope can be concomitantly secured by a cord or lanyard around the patient's neck. The invention discloses novel improvements in data recorder designs specifically related to data collection and analysis of physiological data during sports activity rather than to data collection and analyses of electrocardiographic or other physiological data during clinical patient activity as set forth in co-pending U.S. patent application Ser. No. 09/235,658.

2. Description of the Prior Art

There is an ever increasing need to provide applicable physiological monitoring of cardiovascular performance of individuals undergoing sports activity in major competitive sports such as baseball, football, track, swimming, hockey, water polo, auto racing, and other physical fitness activity in general. There is also a related need for an inconspicuous, hidden monitor that is partially sealed from the immediate environment such that the wearer can perspire heavily and even bathe in a shower without disrupting or disengaging the recording activity. The invention disclosed herein meets the special requirements of a physiological recorder suitable for use in field sports as well as in fitness clubs and country clubs where supervised exercise is offered to individuals of all ages aimed at rehabilitation and weight reduction.

Many and varied long term ambulatory monitoring devices and systems have been developed and marketed over the years with numerous improvements made by applicant herein; most dealing with improved means to provide to the physician, and cardiologist in particular, a higher and higher degree of accuracy in the assessment of a patient's risk of sudden death from heart arrhythmia and other life threatening signal abnormalities. The monitoring process, as applied to electrocardiography, was named after its inventor and pioneer research physicist, Norman J. Holter, President of the Holter Research Foundation of Helena, Mont. Holter's co-inventor and technical assistant on the original Holter concept was Wilford R. Glasscock. The original Holter concept and invention was assigned to Del Mar Engineering Laboratories of Los Angeles, Calif., under technology license from the Holter Research Foundation dated Apr. 19, 1962, and was filed in the U.S. Patent and Trademark Office by assignee, Del Mar, on Jul. 6, 1962. The application issued as U.S. Pat. No. 3,215,136 on Nov. 2, 1965 and taught not only a long term, ambulatory ECG recording technique but also Holter's data reduction and presentation format promoted under Del Mar's U.S. registered trademarks Electrocardiocorder, AVSEPO, and Arrhythmiagraph. The 136 patent specifically taught a means for processing electrocardiographic signals and more particularly to a means for obtaining large quantities of electrocardiac signals and to a means for facilitating the processing and observing in graphic form of large volumes of such signals in a short interval of time.

Based on the presentations set forth in the foregoing 136 Holter patent, Del Mar Engineering Laboratories produced for clinical cardiology the first complete Holter Monitoring Systems in 1963, which immediately inspired research activity of pioneer. research cardiologists: Dr. Eliot Corday, Dr. Lawrence E. Hinkle, Dr. Herman K. Hellerstein and Dr. John S. Gilson. As a result of several years of clinical testing by these physicians of the Holter Monitoring procedure resulting in numerous publications in medical journals on results emanating from test on hundreds of patients, Holter Monitoring was endorsed and recommended as a new revelation in cardiovascular clinical practice, and was eventually adopted as a standard practice worldwide.

Since 1965, a progression of Holter improvement patents have issued over the years, notably that of Oct. 31, 1978, U.S. Pat. No. 4,123,785, "Recorder for Cardiac Signals with Manually Activated Event Marker" by inventors Isaac R. Cherry and Donald L. Anderson of Del Mar Avionics, successor to Del Mar Engineering Labs. The 785 patent disclosed a small, hip/side mounted tape recorder for ambulatory recording of cardiac signals over a twenty-four hour interval and included a clock with visual display and a patient event marker. Cardiac signals were simultaneously recorded on two tracks on magnetic tape wherein the event marker function could also be recorded and activated by the patient to denote the happening of a specific event sensed by the patient that can be easily recognized on play back in relation to heart activity at the time. The 785 Cherry patent was followed by yet many other noteworthy inventions.

The forgoing U.S. patents taught many important developments in Holter Monitoring technology but were yet followed by a series of other prior patents of Del Mar Avionics dealing with Holter Monitoring concepts. U.S. Pat. No. 4,532,934, was issued August 1985, titled "Pacemaker Monitoring Recorder and Malfunction Analyzer", by inventor George J. Kelen, M.D. The Kelen 934 patent disclosed a hip/side mounted magnetic tape recorder which detects and records sequential pacemaker spikes in one channel in a waveform compatible with corresponding ECG signals recorded in a second tape channel. The system further includes an analysis module connected to the playback unit for receiving both the ECG and pacer spike signals and is adapted to play back both channels of information at 120 times recording speed. An analysis module in the recorder has counters to accumulate the number of paced beats and fusion beats. The system is further configured to sense malfunctions, failure to sense, failure to capture, and abnormal bradycardia.

U.S. Pat. No. 5,109,862 issued May 8, 1992 and was titled 'Method and Apparatus for Spectral Analysis of Electrocardiographic Signals,' by inventors George J. Kelen, M.D. and Raphael Henkin, Ph.D. The Kelen 862 patent discloses a signal processing and analysis method and apparatus for plotting and measuring ECG signals where the graphic plots and numeric parameters measured reveal abnormalities of electrical conduction within the heart thought to anticipate abnormal heart rhythm, arrhythmia. The invention employs Fourier Analysis of short overlapping segments of ECG signal to create a three-dimensional electrocardiogram map.

U.S. Pat. No. 5,205,295, issued Apr. 27, 1993 "Method and Apparatus for Holter Recorder with High Resolution Signal Averaging Capability for Late Potential Analysis," by inventors Bruce Del Mar and Isaac R. Cherry. The Del Mar 295 patent discloses a method for digital signal averaging of selected signals and storing for future playback. The averaged signals, several times per hour in a 24-hour period, are correlated with previously defined correlation coefficients to yield summated results that have eliminated non-repetitive noise. Information so accumulated enable micropotential analysis of cardiac electrical activity.

Since 1996 digital data storage capacity in lightweight disc drives and printed circuit card, flash memory components has progressed in production to the point where solid-state ambulatory physiological recorders can be made at reasonable cost. Such recorders offer an advantage over prior art ambulatory physiological tape recorders because digital recorders have no moving parts and no need for separate analog-to-digital data conversion. Solid-state recording now represents a formidable improvement in the art of ambulatory physiological recording.

Long-term ambulatory physiological and Holter recorders have been conventionally worn in a protective pouch slung by straps over the shoulder outside the clothing or hung on a person's belt, again outside the clothing. Many problems and inconveniences can occur while wearing such conventional ambulatory physiological recorders, especially because of the necessary prolonged, continuous recording times involved. Dressing and sleeping become troublesome due to the long wire harness required on existing recorders. Electrodes often get pulled off the chest by the wire harness during sleep and active physical activities. The recorder may also receive rough treatment from dropping to the floor or exposure to other hostile environments. With the invention disclosed herein, compactness and simplicity replace a variety of components and complication. With the new invention disclosed herein, exercise, including walking and running, is unrestricted. The daily routine of sleeping, dressing and bathing in a shower need not change! And, for the clinician, this invention can create more reliable long-term monitoring of physiological signals. Of special note, the ambulatory data recorder of the invention incorporates design features especially suited to long term wear under wet or dry conditions wherein there may be a broad array of arm and leg motion with or without protective clothing covering the athlete and the monitor.

SUMMARY OF THE INVENTION

As will be more particularly described herein, the ambulatory data recorder of this invention utilizes compact, contiguous, and high continuity integrated circuitry; A-to-D converters; a CPU operating system; a physiological sensor elements; acceleration detector element; printed circuit, flash memory and DC power to record at least one, but preferably three, channels of physiological kinetic data, with optional event marking and optional activity monitoring, as well as means to program specific periods of recording with or without data compression. All the foregoing functions and elements are sealed within a compact recorder housing disposed within an envelope or inverted pouch protecting the recorder from water and environmental contaminants. In one embodiment of the invention, the recorder is provided with at least one adhesive skin patch, but preferably four, that hold the monitor on the patient's chest with the option of a backup security lanyard hung around the patient's neck in the manner is of a necklace to also support the recorder. In a second embodiment, the recorder housing is disposed within a sealing envelope or inverted pouch, wherein said envelope is attached by at least one, but preferably a pair of swivel type adhesive electrode elements to enable less restricted body movements. The recorder system has multiple sensor attachments and serial and parallel output ports to download recorded data for digital analysis and display of a full disclosure or summary data report on a conventional Personal Computer (PC) or other digital retrieval system.

OBJECTS OF THE INVENTION

It is a primary object of the invention to provide an ambulatory physiological data recorder designed to give information on cardiovascular electrophysiology together with a measure of corresponding physical activity on athletes and fitness performers during the practice of their sport.

It is a another general object of the invention to provide for a long term, ambulatory physiological data recorder design to obtain more complete and reliable ambulatory physiological recordings by providing a self contained recorder device mounted on the patient's skin directly adjacent the organ or system to be monitored, particularly the heart, but not necessarily limited thereto, thereby diminishing the length of the body attached sensors and leads thereto.

It is yet another substantial object of the invention to enable a physician to attach a compact recorder system to a patient in a manner that is out of sight and inconspicuous, as well as more convenient and comfortable to wear.

Another object is to provide for higher electrical continuity of sensor contacts made possible by the simplicity of wearing this novel recorder at the signal source and avoiding recording failures or introduction of artifact attributed to loose rigging of lengthy leads and sensor apparatus on the body;

Another object is to increase recorder continuity and reliability by utilizing a double sealing, adhesive ring around each electrode sensor;

Yet another object of the invention is the provision for recording ambulatory physiological signals in an unseen, covert fashion under the patient's clothing;

Still another object is to provide an independent ambulatory physiological recording means and process that does not need to change patient's daily routine, e.g. exercising, bathing, getting dressed, by placing the recorder within a semi sealed envelope or inverted pouch to ward off water from while bathing in a shower or from a heavy perspiration environment;

Another object is to provide ambulatory physiological recording without restriction to daily exercise or position of the body or limbs, including walking and running;

Yet another object is to reduce the cost of obtaining ambulatory physiological recordings for the patient, the medical practitioner, and the government by incorporation of micro miniature, digital solid state electronics;

Still another object of the invention is to provide an ambulatory physiological recording system wherein body activity, acceleration sensors located directly within the recorder can provide information on body orientation, activity and acceleration simultaneously with other sensor data to measure the relationship between physical activity and sensor data throughout the recording period;

Another object is to provide an ambulatory physiological recorder that is pliable and comfortable to wear by having flexibility to fit the contours of the body;

Another object is to utilize a lanyard extending around the athletes neck to lend additional support of the monitor suspended over the body organ, e.g. the heart, to be monitored; and Yet another object is to provide a readily available ambulatory physiological recorder for short-term recording of body signals while undergoing an informal treadmill or improvised stress test using a limited number of sensors. The period of recording may be short, but the data analysis can be reported quickly from the digital write out device, already available for other related purposes. Such a stress test can be conducted in the physician's office as an adjunct to other long-term physiological monitoring tests.

DETAILED DESCRIPTION OF A PREFERRED EMBODIMENT

Figure 1:
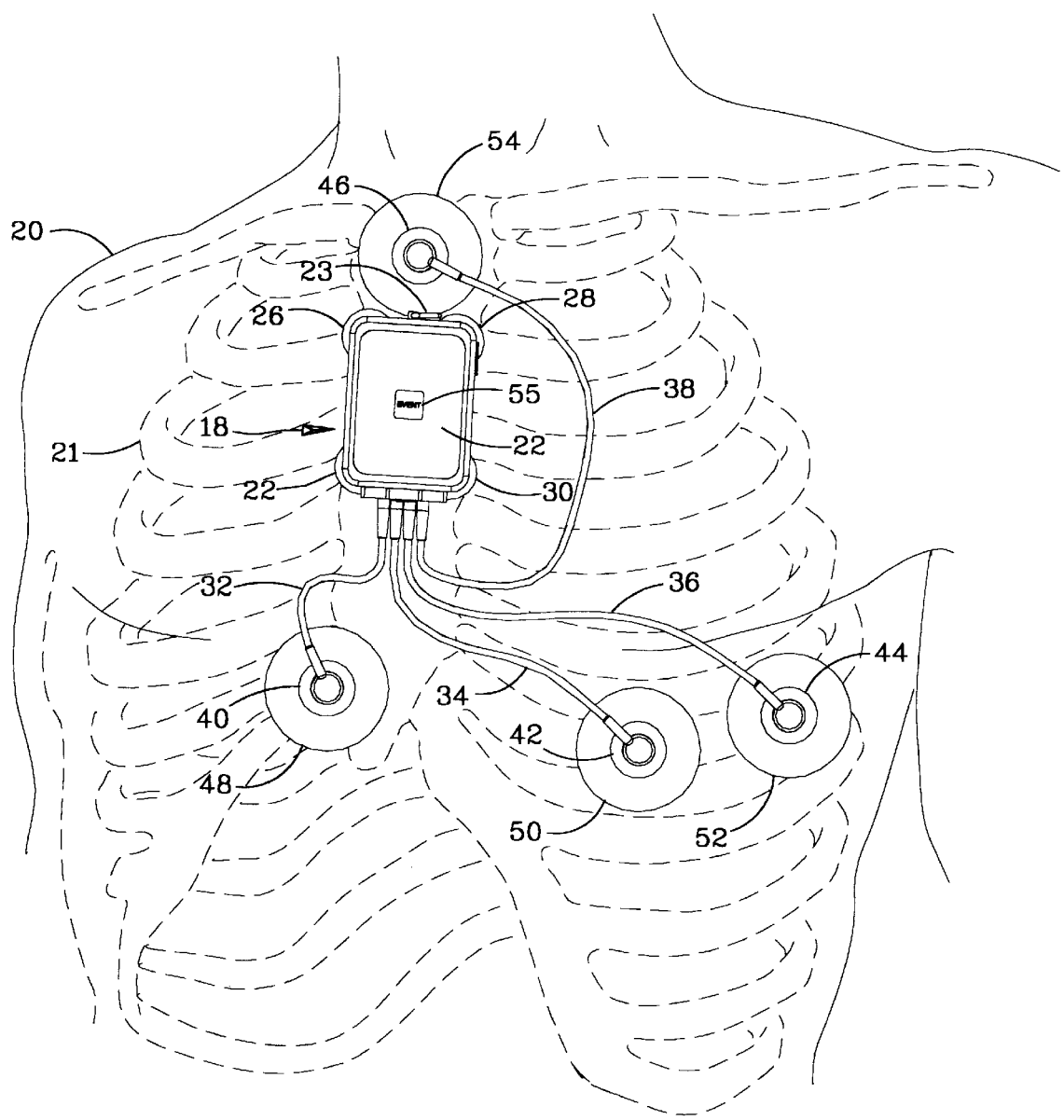
FIG. 1 illustrates a pictorial view of the ambulatory physio-kinetic monitor mounted on a patient by four conventional, inactive electrode adhesive patches with imaginary lines delineating the rib cage for accurate placement of electrode sensors.

The following description of a preferred embodiment describes a specific embodiment of the invention concept in great detail as an enabling disclosure. It will be appreciated, however, that the scope of the invention concept may extend to many obvious and similar other embodiments and will be limited by the depth and breadth of the claims alone and not by the description of the preferred embodiment herein. Only when there is an ambiguity of the terms or meaning of a claim as drafted will the description be necessary to interpret the claims. It will be further understood that like numerals on different figures of the Drawing refer to the same element on each succeeding figure of the drawing.

Figure 2:
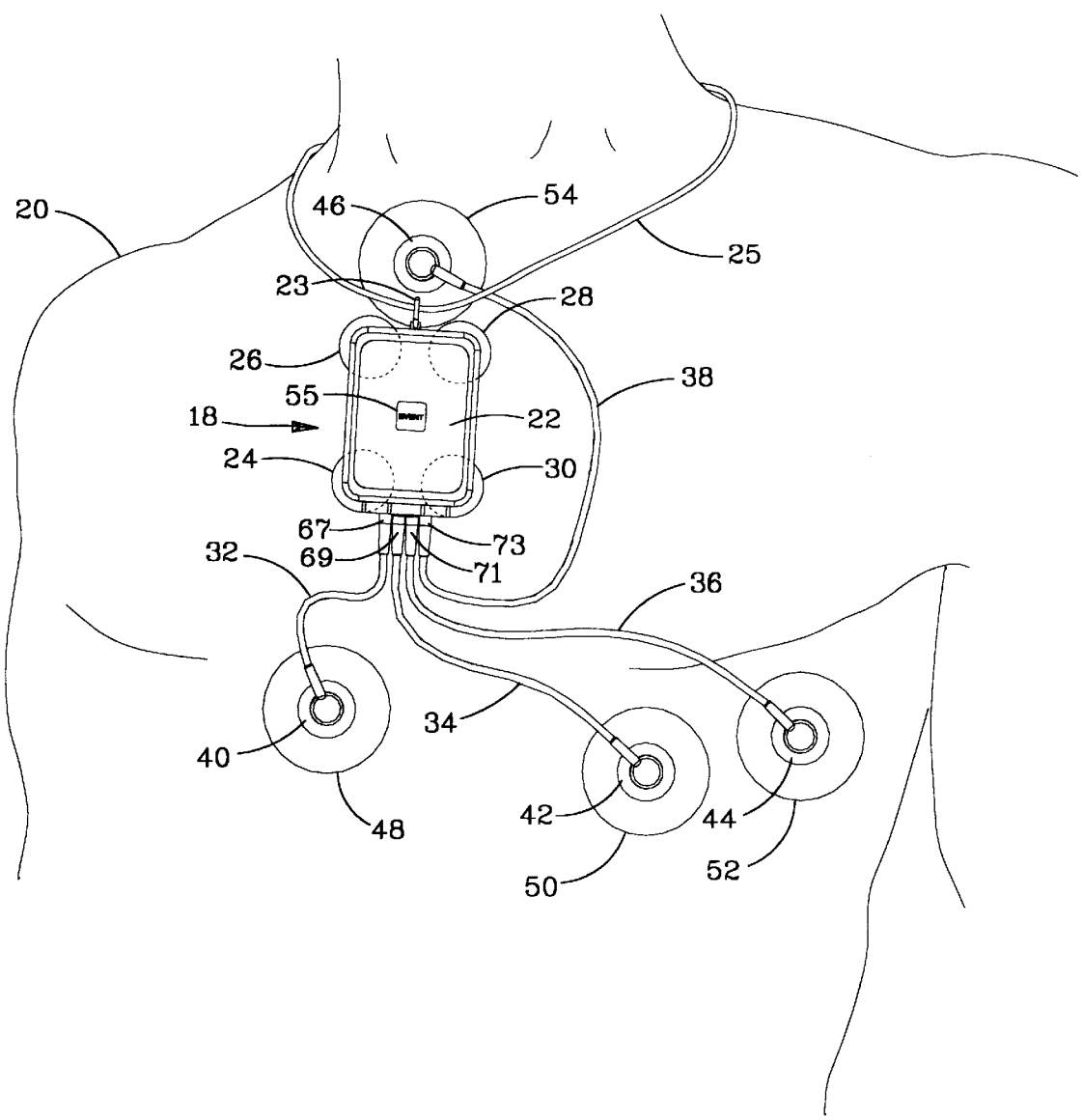
FIG. 2 illustrates a pictorial view of FIG. 1, without rib cage for clarity of view, and with the optional lanyard slung around the patient's neck for additional support of the monitor in very active physical activity.

FIGS. 1 and 2 illustrate a frontal view of the orientation of one embodiment of the ambulatory physio-kinetic monitor mounted on a patient's chest and adapted for use as an ambulatory electrocardiograph (ECG) monitor. The monitor 18 is mounted on a patient's chest 20 in an area immediately adjacent the area over the heart within the patient's rib cage 21, illustrated by hidden lines. Rib cage 21 is illustrated in FIG. 1 for assisting in accurate placement and attachment of the monitor and electrode sensors extending therefrom. The invention monitor consists of a square or rectangular shaped, environmentally sealed box or enclosure, about the size of a package of cigarettes, designated as monitor housing 22, and is provided with four conventional, non active electrode, adhesive pads, 24, 26, 28, and 30 for comfortable attachment of monitor housing 22 directly to the skin of a patient to be monitored. Although housing 22 is illustrated in the preferred rectangular shape, it can be appreciated that housing 22 could be virtually any shaped polygon, triangle, square, rectangle, pentagon, hexagon, circle, etc. Referring to FIG. 2, housing 22 is also provided with a second or alternative mounting means in the form of a triangular ring 23, disposed on the upper end of housing 22. Ring element 23 may be folded flat against housing 22 for packaging purposes, as illustrated in FIG. 1, and is raised for use, as illustrated in FIG. 2. A comfortable fitting lanyard or neckband 25 is caused to pass through ring element 23 and is secured around the neck of the patient. Although the neck band 25 and ring 23 combination is alone sufficient to support monitor housing and attachments thereto, the neck band 25 is primarily designed as a safety precaution to be able to "catch" the monitor housing 22 from falling off the body on the remote occasion that one or more of the adhesive pads 24 through 30 should disengage and fall off. Because there may be occasions where adhesive pads 24 through 30 cannot be used to support the monitor 18 by application to the patient's skin directly due to patient skin sensitivity or allergic tendencies, the adhesive pads 24 through 30 may be detached and the mounting ring 23 and neck band 25 mounting means my be used alone. It should be noted, however, that said inactive electrode adhesive pads serve a two fold function; the pads not only mount the monitor housing 22 to the patient's chest, but they also hold the housing and electrical leads thereto in a relatively stationary position. If housing 22 and attached electrode leads are allowed to fly about or even move a little, electrical discontinuities and muscle artifact may well occur between electrodes and housing, thereby causing incorrect or difficult to interpret data readings. Of even greater significance, however, is the fact that the motion detector, not shown, is disposed on the PCB within housing 22. If housing 22 is allowed to fly wildly about the patient's chest, no meaningful kinetic/motion readings could be taken and correlated with ECG readings. Therefor, although the neck band, lanyard 25 alone is sufficient and adhesive pads 24 through 30 alone are sufficient to support housing 22 over the patient's chest, it is envisioned and recommended that both adhesive pads 24 through 30 or at least one of said pads, be utilized along with neck band, lanyard 25.

Figure 2A:
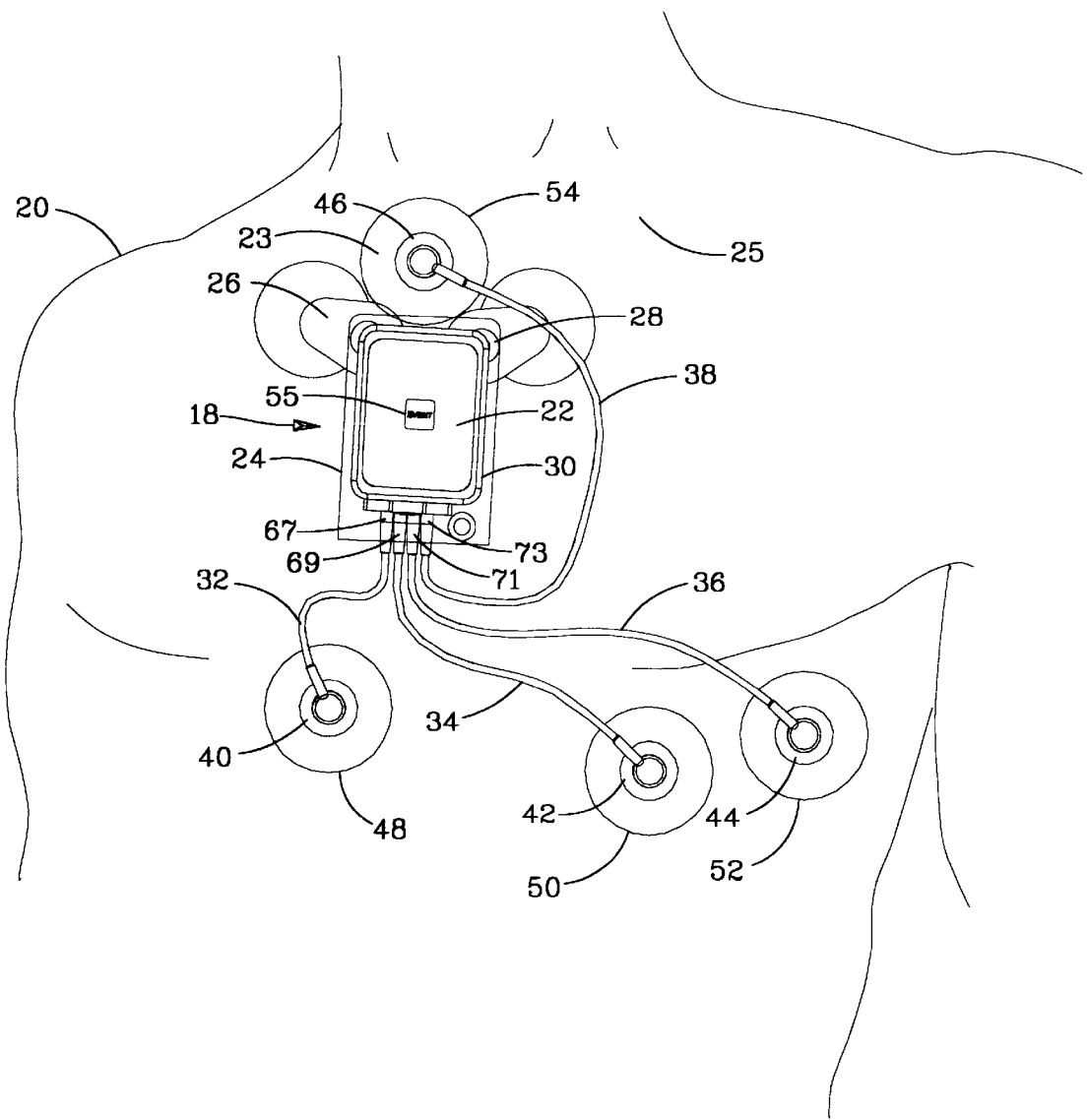
FIG. 2a illustrates a pictorial view of the ambulatory physio-kinetic monitor disposed within a water repellant, protective and transparent envelope or inverted pouch that, in turn, is affixed to the wearer's chest by a pair of swivel type adhesive electrode patches.
Figure 2B:
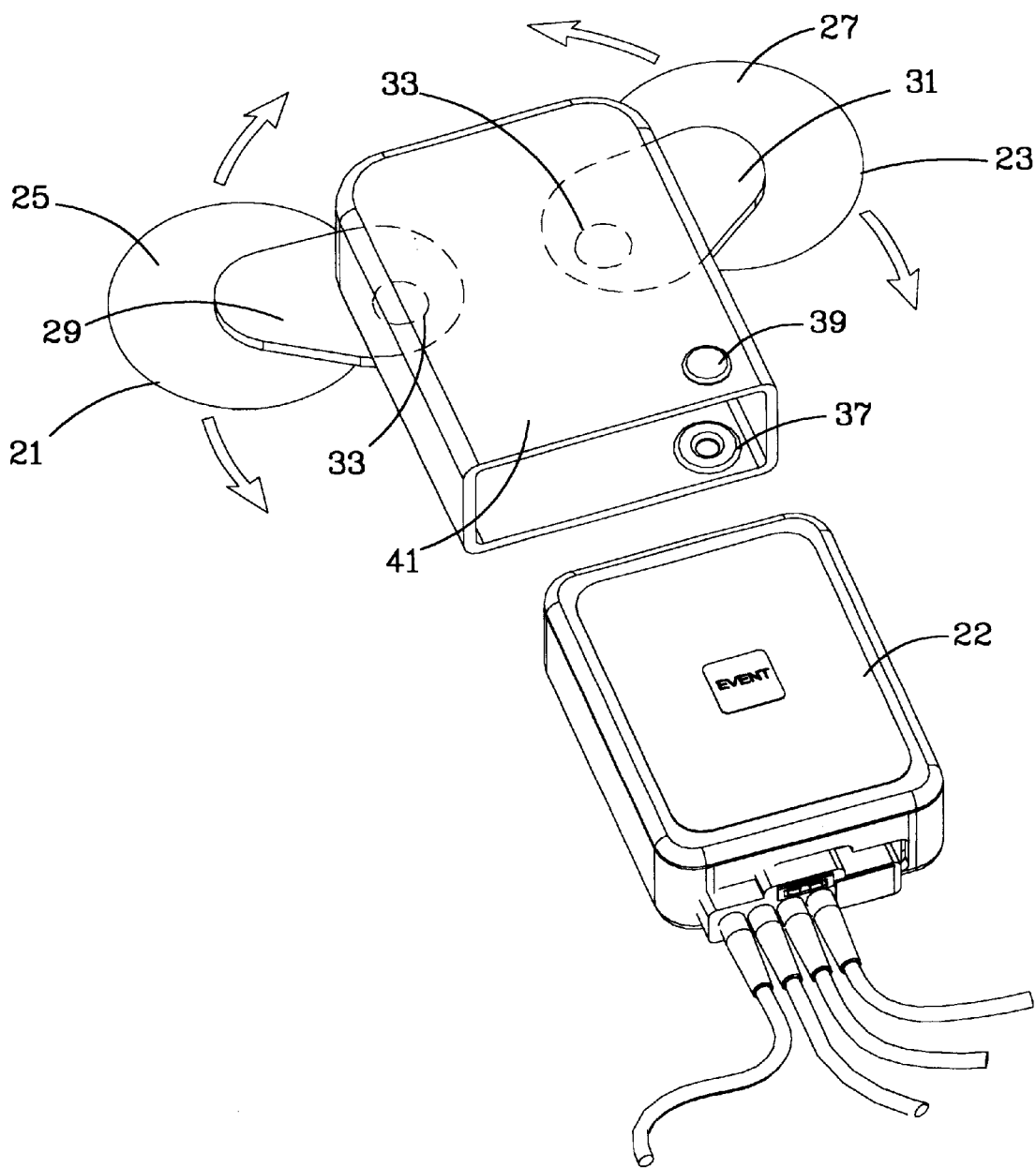
FIG. 2b illustrates a pictorial view of the recorder of FIG. 2a withdrawn from the transparent envelope.

An alternate embodiment of the invention is illustrated in FIGS. 2a and 2b. IN the alternate embodiment, the four inactive electrode adhesive pads 24–30 have been deleted from housing 22 and housing 22 is configured to be inserted into a water repelling envelope or inverted pouch 19, which in turn is attached to the patient's body by a pair of conventional inactive swivel electrode adhesive pads 21 and 23. As indicated in FIG. 2b, swivel adhesive pads 21 and 23 are oblong in construction and are further structured with first oblong adhesive pads 25 and 27 and second oblong adhesive pads 29 and 31, each of which are permitted to somewhat freely pivot or rotate about the male/female snap on electrode elements 33 and 35, respectfully.

Recorder housing 22 is confined within envelope 19 by male/female snap on elements 37 and 39, respectfully, that substantially close off the opening 41 of sealing envelope 19, to safely confine recorder housing 22 therein. It should be noted that the swivel pad electrode attachment elements 33 and 35 allow much more comfort and freedom of body movement with the recorder attached than did previous adhesive electrode attachment devices.

In the preferred embodiment, the ECG monitor housing 22 is provided with at least four electrical leads; a first, second and third positive electrical leads, 32, 34, and 36, respectively, and a single, common or negative lead 38. It would be obvious to add additional leads for additional physiological data; however, the invention delineated herein strives for simplicity in design and micro compactness in packaging. Each lead provides ECG input from conventional, electrolyte filled, first through fourth electrodes, 40, 42, 44, and 46, respectively, each said electrode attached to the patient's skin by electrode adhesive pads 48, 50, 52, and 54. Data from first, second and third positive leads is recorded on a first, second and third channels, respectively, discussed more fully infra. In the preferred embodiment, kinetic activity data is periodically recorded on channel 3 also along with the relevant ECG data for channel 3. An event button 55, which will be addressed more completely infra, is conveniently disposed flush with the exterior surface of monitor housing 22 in order that the patient wearing the ECG monitor may conveniently and inconspicuously push button 55 to note and mark a particular event occurring during the monitoring period.

Figure 3:
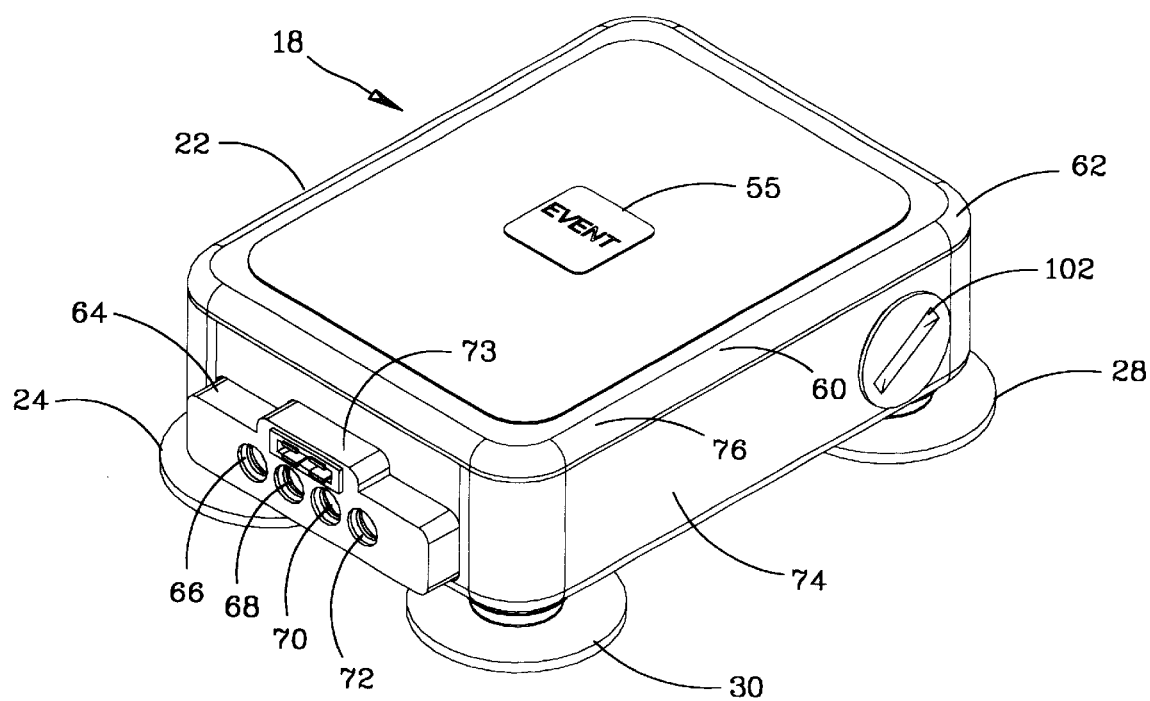
FIG. 3 illustrates a solitary, perspective view of the self contained, ambulatory physio-kinetic monitor with four snaps on inactive electrode adhesive pads.
Figure 4:
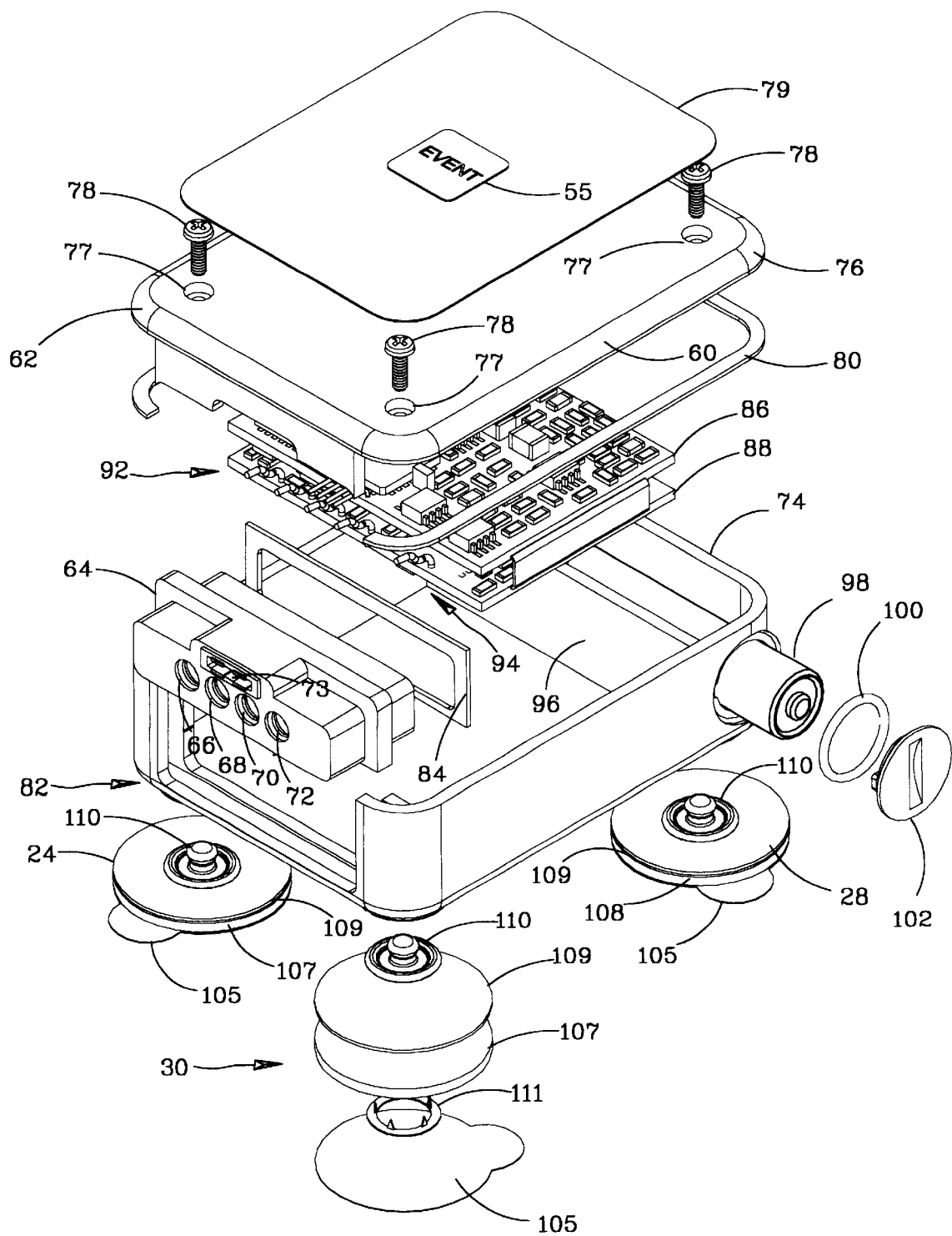
FIG. 4 illustrates a topside, perspective, exploded view of the ambulatory physio-kinetic monitor with detached snap on adhesive pads.
Figure 5:
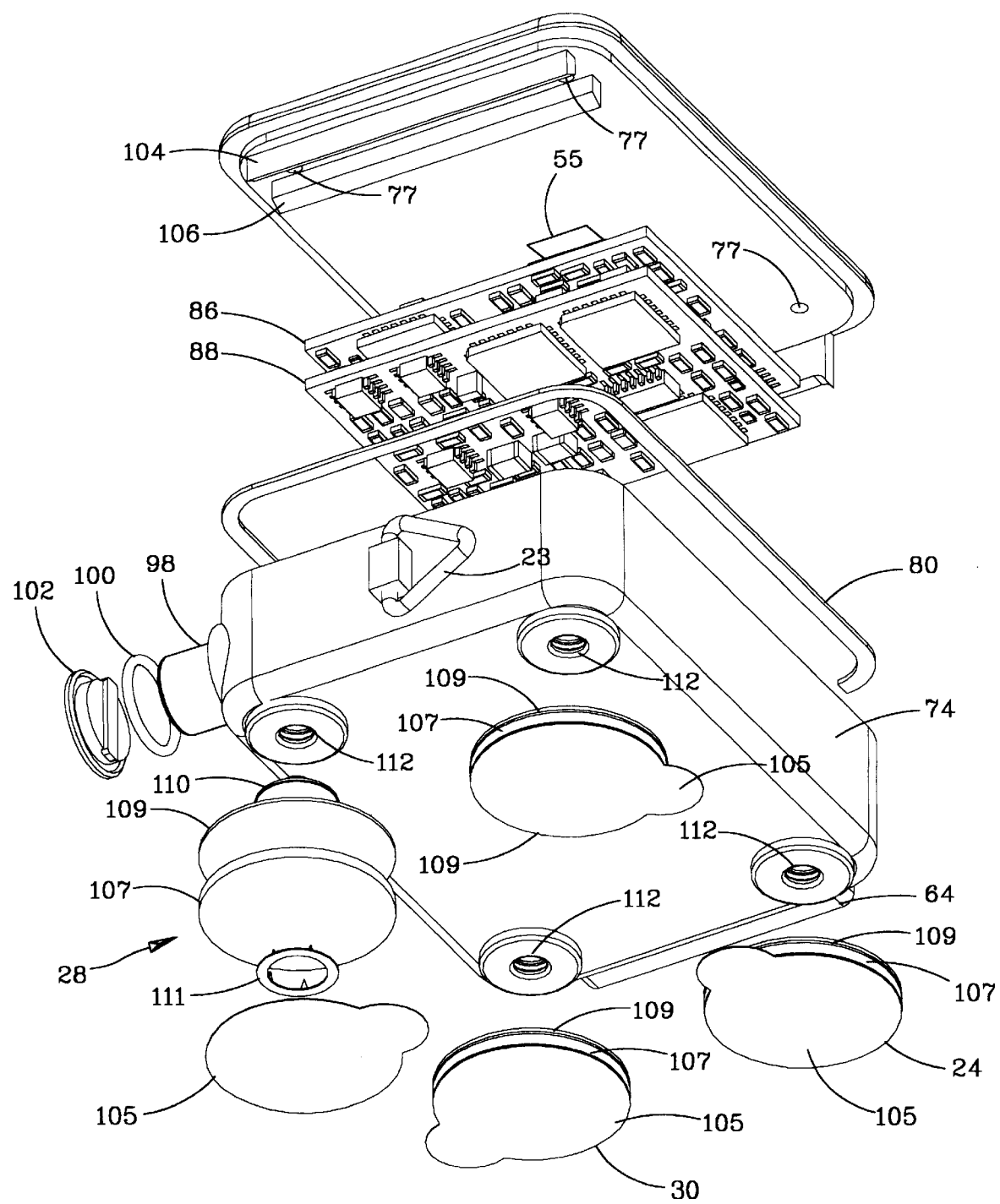
FIG. 5 illustrates a bottom side, perspective, and exploded view of the ambulatory physio-kinetic monitor with detached snap on adhesive pads.

Referring now to FIGS. 3, 4, and 5, a perspective view of ECG monitor housing 22 is more clearly illustrated, wherein FIG. 3 depicts the housing alone, FIG. 4 illustrates a top exploded view of housing 22 and FIG. 5 illustrates a bottom exploded view thereof. All the hardware and firmware components of the recording elements of the monitor, excepting, of course, electrodes and electrical leads are totally encapsulated in the environmentally sealed and water proofed monitor-housing 22. Monitor housing 22 consists of a plastic molded, rectangular base 74 covered by a plastic molded lid 76 that is attached to base 72 by four screws 78 and is sealed to the base via a rubber grommet 80 that circumvents the periphery of lid 76. Input/output interface 64 is configured to snugly fit within a cutout 82 of base 74, and is environmentally sealed water tight by an input interface seal 84 circumventing the periphery of interface 64 and attached to the inside wall of base 74. Housing 22 is designed with curved circumferential edges 60 and corners 62 to avoid sharp edge injury or irritation of the device with the patient's body, and since the invention monitor is specifically designed to be worn out of sight and under the patient's clothing, the curved surfaces also inhibit catching or tearing of clothing worn over the monitor. Also for ease and comfortable wearing, housing 22 is preferably constructed of a soft, pliant, lightweight, and rugged material, for example a soft plastic or soft rubber. Alternatively, housing 22 may be constructed of harder materials if necessary for durability and covered with a soft textured material such as Santoprene, manufactured by Advanced Elastomer Systems of Akron, Ohio.

The plastic or hard rubber input/output interface 64 is configured with four cylindrical, sealed, "male contact" receptacles, input receptacles 66, 68, 70, and 72 for insertion therein of four cylindrical "female" electrical input contacts 67, 69, 71, and 73 for leads 32, 34, 36, and 38, respectively, illustrated in FIG. 2. An output receptacle 73 is configured for receipt of a universal serial buss (USB) element. Once cardiovascular data and related kinetic data is accumulated in flash memory over a period of time, the thusly accumulated data is downloaded from the physio-kinetic monitor to a PC or other data analysis device.

Figure 6:
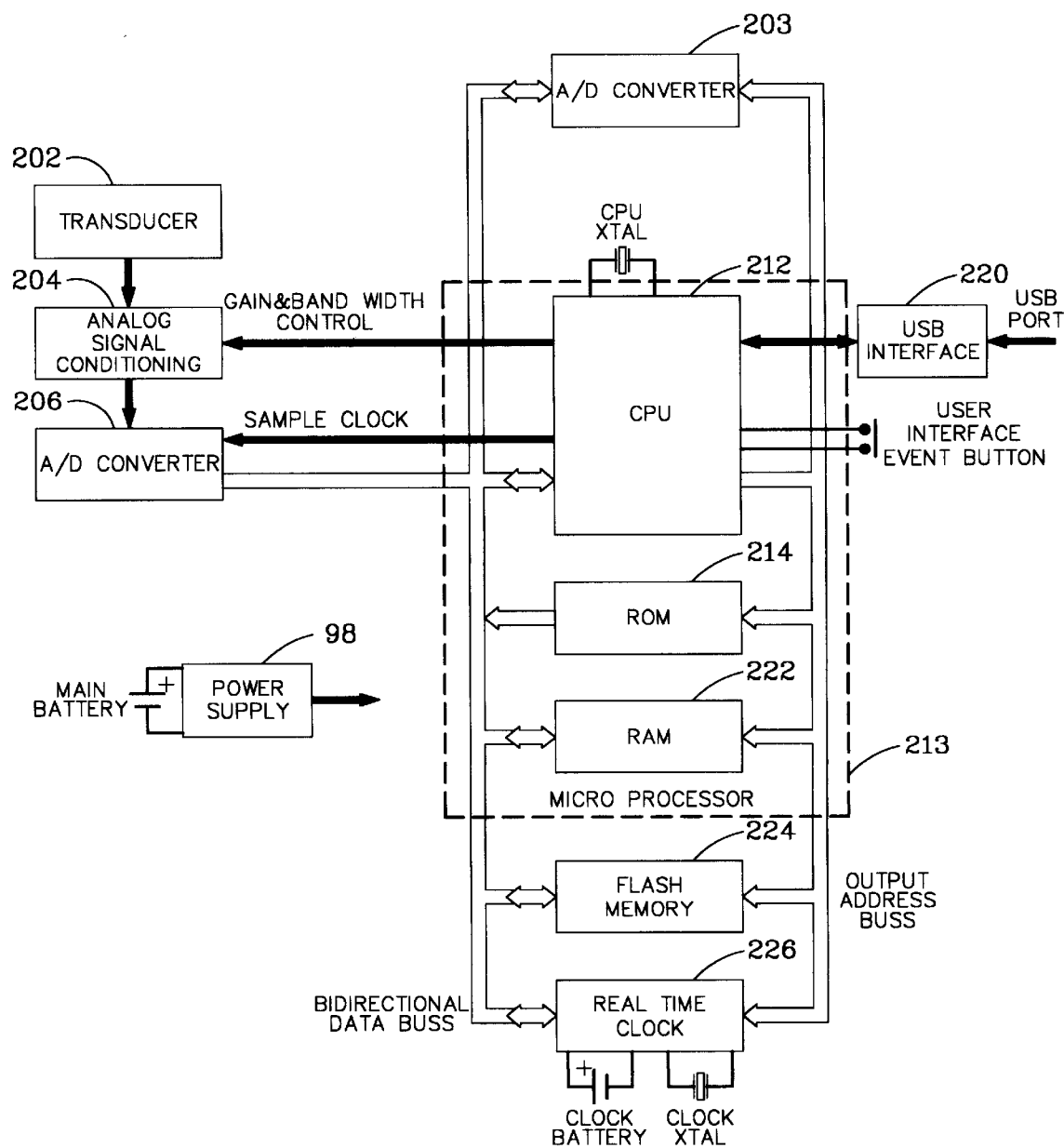
FIG. 6 depicts a block flow diagram of the PCB components and functions of the monitor.

Referring particularly to FIGS. 5 and 6, it can be observed that all electronic components contained within housing 22 are assembled on a first and second dual sided and parallel printed circuit boards (PCB) 86 and 88 coupled together electronically via PCB buss 90. PCB input leads 92 and output leads 94 couple PCB 88 to input/output interface 64. PCB 86 and 88 are configured to fit snugly within housing 22 base 74 and is environmentally enclosed therein by lid 76 and seal 80. Lid screws 78 secure lid 76 to base 74 through appropriate screw holes 77; a protective, decorative cover 79 hides screw heads thereunder and also provides a mounting platform for event switch 55 discussed infra.

The system power supply consists of a battery compartment 96 containing a pair of AA batteries 98 in tandem. Batteries 98 are protected within compartment 96 by a battery seal 1 00 and battery compartment door 102. Batteries 98 are held fixedly in place in battery compartment 96 by a pair of battery restraint rails 104 and 106 molded on the underside of lid 76.

All electrode adhesive pads 24–30, 48–54, 21 and 23, are uniquely constructed and designed to be throw away items of the monitoring process; i.e. the adhesive pads are the only elements of the monitor that have intimate contact with the patient's body. Such materials, once used, should not be applied to another patient or athlete's body. Each adhesive pad 24–30 is designed with a peal away plastic or paper cover 105, that protects a soft sticky pad 107, a flexible plastic shield 109 and a top side pimple 110, male insert, for convenient attachment to a respective dimple 112, female receptacle, of housing 22. Pimple 110 is attached to plastic shield 109 and sticky pad 107 by a crimping element 111. By application of four of these uniquely constructed adhesive pads to mount the monitor to the patient's body, a firm yet flexible, body contoured mounting platform is derived.

Referring now to FIG. 6, a block flow diagram of the functional electronic components of PCB's 86 and 88 is delineated. The block flow diagram in FIG. 6 is designed for a very small and compact, lightweight digital recorder. The recorder circuit on PCB's 86 and 88 in FIG. 6 is designed to accommodate and record a variety of physiological signals. Monitor 18 is specifically designed with the concept to be fully "self contained" and preferably mounted immediately adjacent the organ or system which is to be monitored to, among other reasons, diminish lengthy electrical leads and related artifact and discontinuity; the recorder circuit is powered by an internal battery 98. Monitor 18 physically possesses its own attached sensor electrode input devices, data storage, data manipulation (microprocessor), and data output. The circuit is designed to operate in an ambulatory environment for a recording period of at least twenty-four (24) hours. The transducer, electrode sensor, analog signal conditioning and sampling rate can be changed to meet the requirements of the data to be recorded.

The transducers 202, i.e. positive electrode sensors 40, 42, 44 and common negative/ground electrode 46, utilized in any particular application will depend on the application of varying bioelectric potentials, such as electrocardiograph (ECG), electroencephalograph (EEG), electromyograph (EMG), etc. Transducer 202 would be appropriate skin contact electrodes such as electrode sensors 40, 42, 44 and 46; however, for acceleration, activity or body movement sensors, the transducer would be acceleration sensors; for pressure recording, the transducer would be a pressure transducer; and for skin temperature recording, the transducer would be a thermal type transducer. In the specific embodiment at hand, an acceleration sensor 203 mounted on the PCB 88 appropriately detects movement.

The activity monitor, accelerometer is a device to augment traditional Holter ambulatory ECG monitoring activity by use of a patient motion sensing module. The output of the motion sensing device is an analog signal, as is the ECG signal, that represents the "G" (gravity) acceleration on the body. The signals are conditioned to be in the signal level range for typical Holter recording technology and are input to channel 3. The patient's activity can be viewed or printed out using a Holter scanner I conjunction with relative ECG strips, trends or full disclosure printouts. Typical Holter scanners offer trends of heart rate, ST levels and arrhythmia. The trends can be combined with. patient activity trends to show possible correlations between physical and emotional stress.

The addition of this type augmentation activity device to Holter recorders allows the physician to better derive the status or conditions that are otherwise difficult to obtain. By combining the simultaneous presence of ECG during normal activity the level of activity and its correlation with ECG changes can be observed by the reviewing physician. The purpose of this device is to augment the information that a physician would get over other Holter recordings to help in the diagnosis of heart arrythymias and ST depression of the ECG associated with stress. This device in no way suggests an outcome or treatment. It provides additional information only that can be evaluated or discarded by the physician.

Transducer 202 feeds a data signal into an analog signal conditioner 204, the exact elements of which will depend on the transducer type and the recording characteristics desired. These characteristics would include sample rate, resolution, and amount of data to be stored. The signal conditioning function is further characterized by the type of input, the necessary gain, the bandwidth, the signal to noise ratio, the maximum input signal, the maximum output signal, common mode rejection and the operating environment requirement. The primary function of analog signal conditioner 204, however, is to amplify transducer 202 output signal to the level required by an analog to digital converter 206.

Analog to digital converter (A/D) 206 primary function is to sample analog signals on each cycle of a sample clock 208. The A/D output is a digital value represented by one's and zeros on a set of parallel lines. In the preferred embodiment, the typical number of lines or bits would be eight (8). A/D converter 206 is in turn connected by an eight bit data bus 21 0 to a central processor unit (CPU) 212 within microprocessor chip 213.

Central processor unit 212 in the preferred embodiment is a standard CPU used in micro processor and controller environments. CPU 212 function is to read instructions stored in a read only memory (ROM) 214 and to execute those instructions. CPU 212 is the heart of any stored program controller. CPU 212 receives and outputs data through a bidirectional data bus 216 through parallel ports, serial ports and other undefined control pins. An output address buss 21 8 determines which of the devices connected to data bus 216 is to receive data currently on data bus 216. The address also determines from which device CPU 212 will read data. Other control lines determine weather the data is being determined an output or an input to CPU 212 over data bus 216.

Read only memory (ROM) 214 stores program instructions to control operation of CPU 212. The program instructions stored in ROM 214 is referred to as the embedded program code. Several different programs could be stored in ROM 214. An input by an operator through a universal serial bus port (USB) 220 could determine which one of the programs will be executed. Size of memory 214 will vary with the particular microprocessor used; often in the range of 1 k to 64 k bytes, but typically 16 k bytes in the present application.

Random access memory (RAM) 222 is used by the program executed by CPU 212 for temporary storage of data. Typical use of RAM 222 is as a scratch pad memory, buffer memory and program stack.

Flash memory 224 is a type of nonvolatile memory used in digital devices to store large amounts of data in a small volume. Some of the properties of this type of memory are large volumes of data that can be stored in small chips, e.g. 8 megabytes in a chip 20×12.7 mm. Power can be removed from the device and date will be retained. Data must be written to and read from the memory in blocks of data, typically in 512 byte segments; not a very fast memory.

A built in real time clock 226 makes effective system time and data correlation of data digitized for storage.

Figure 7:
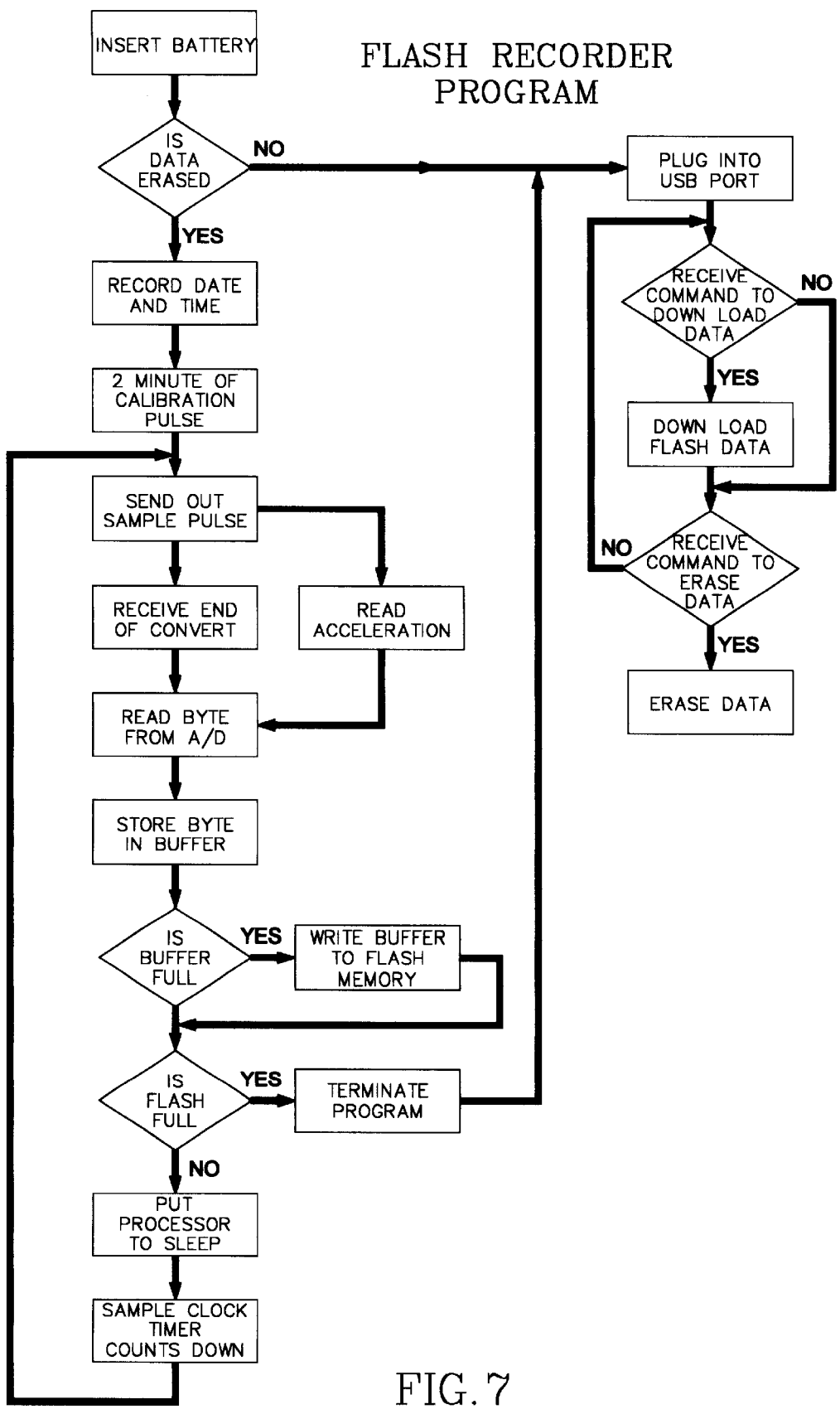
FIG. 7 depicts a block flow diagram of the software recording process of physiological data concomitantly with kinetic data.

Referring now to FIG. 7, a flow chart of the software/firmware operation of the ambulatory physio-kinetic monitor succinctly delineates the logic process for recording data byte by byte. Briefly when the recorder is first powered on and calibrated then mounted onto a patient, data is received from a transducer 202, signal conditioned 204, A/D 206 converted to digital, passes into microprocessor unit 213 to CPU 212 byte by byte to be stored in a temporary buffer until full at which time the accumulated data bytes are passed to flash memory 224 for a predefined recording period. At the end of the recording period or when flash memory is full, data is passed out USB 220 to for example a personal computer (PC) for later analysis and evaluation. The recorder is then physically cleaned and electronically cleaned, data erased, and set up for another patient recording session.

Figure 8A:
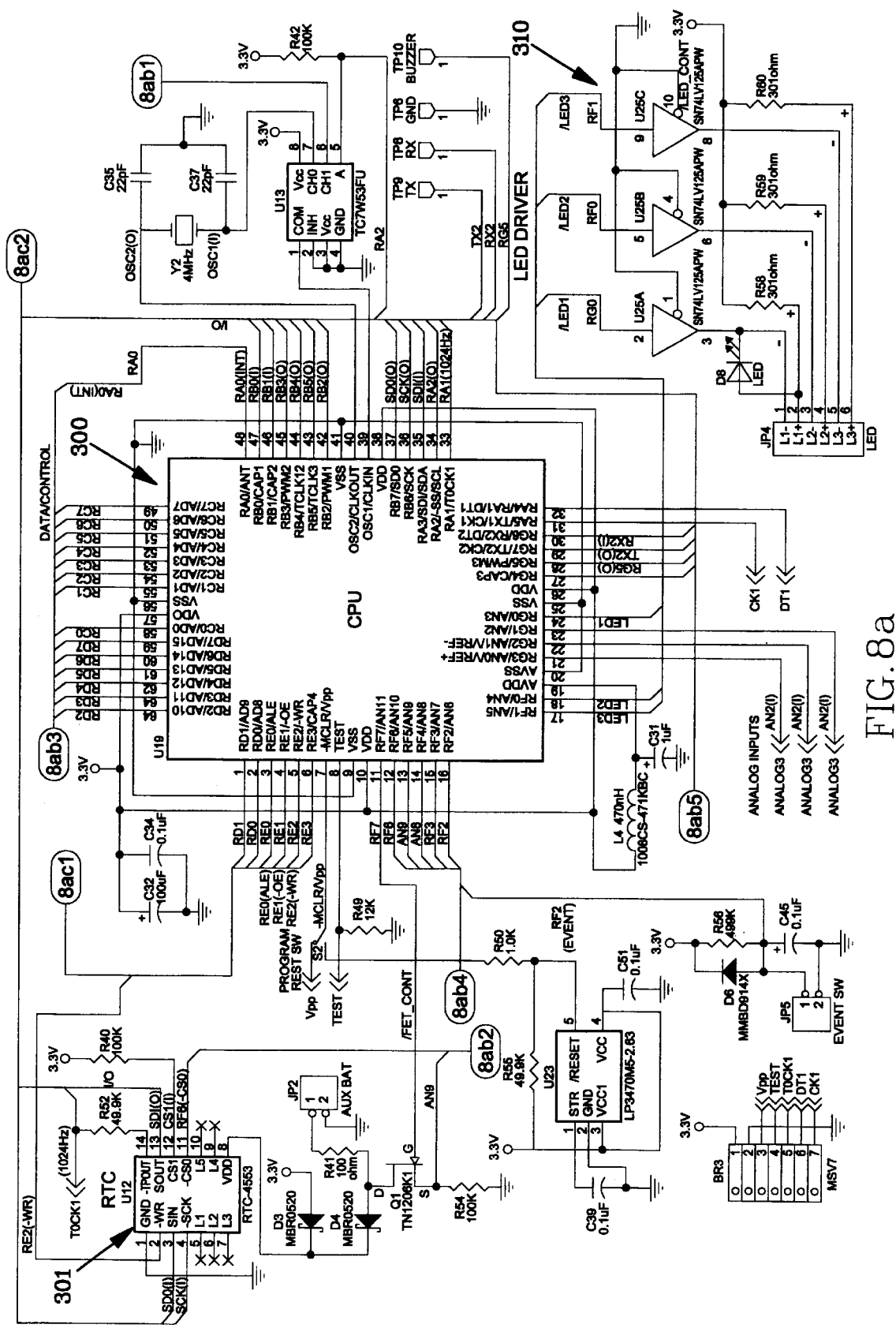
FIG. 8 depicts an electronic schematic of the microprocessor controller circuit on the PCB.
Figure 8B:
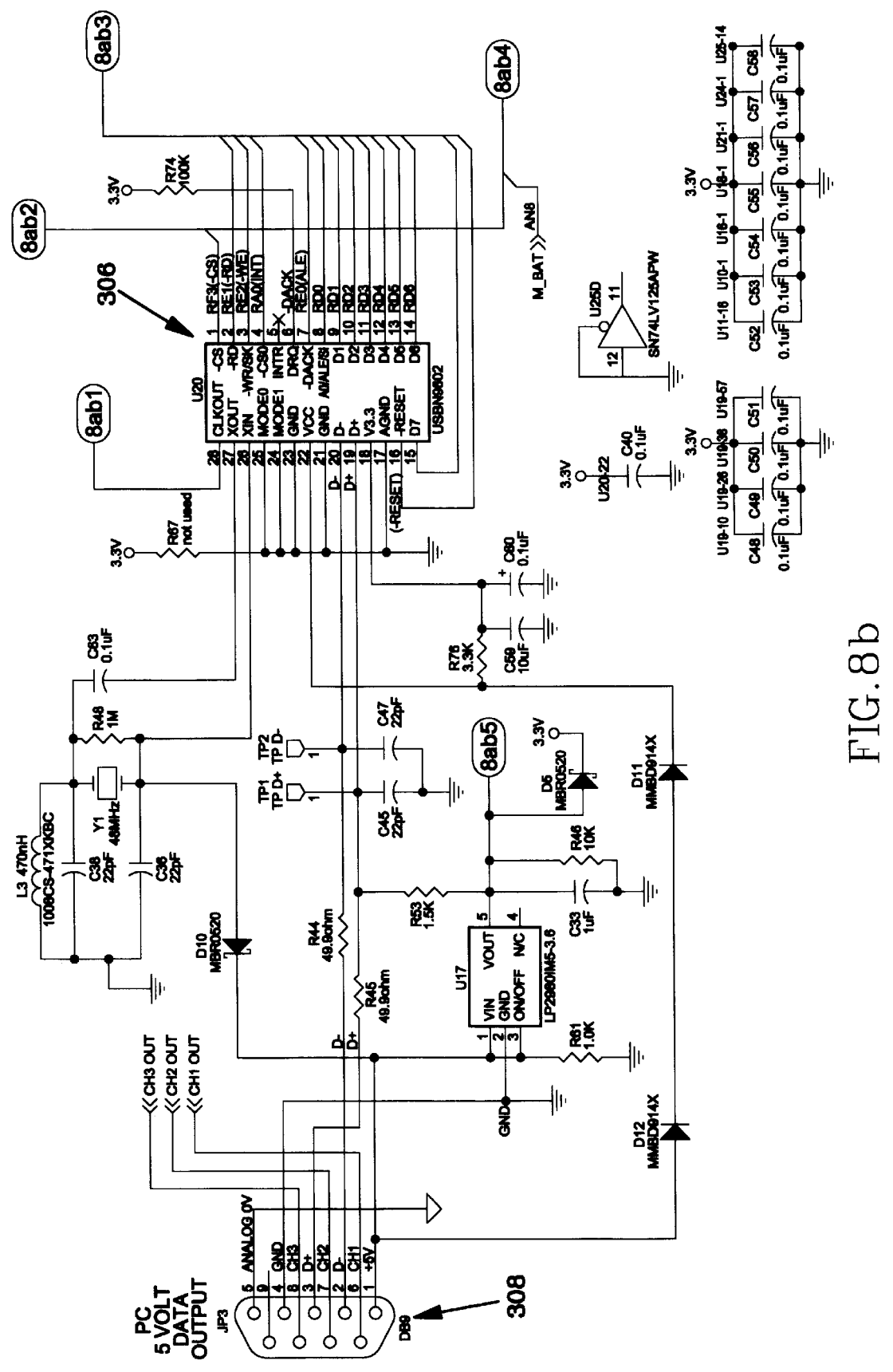
Figure 8C:
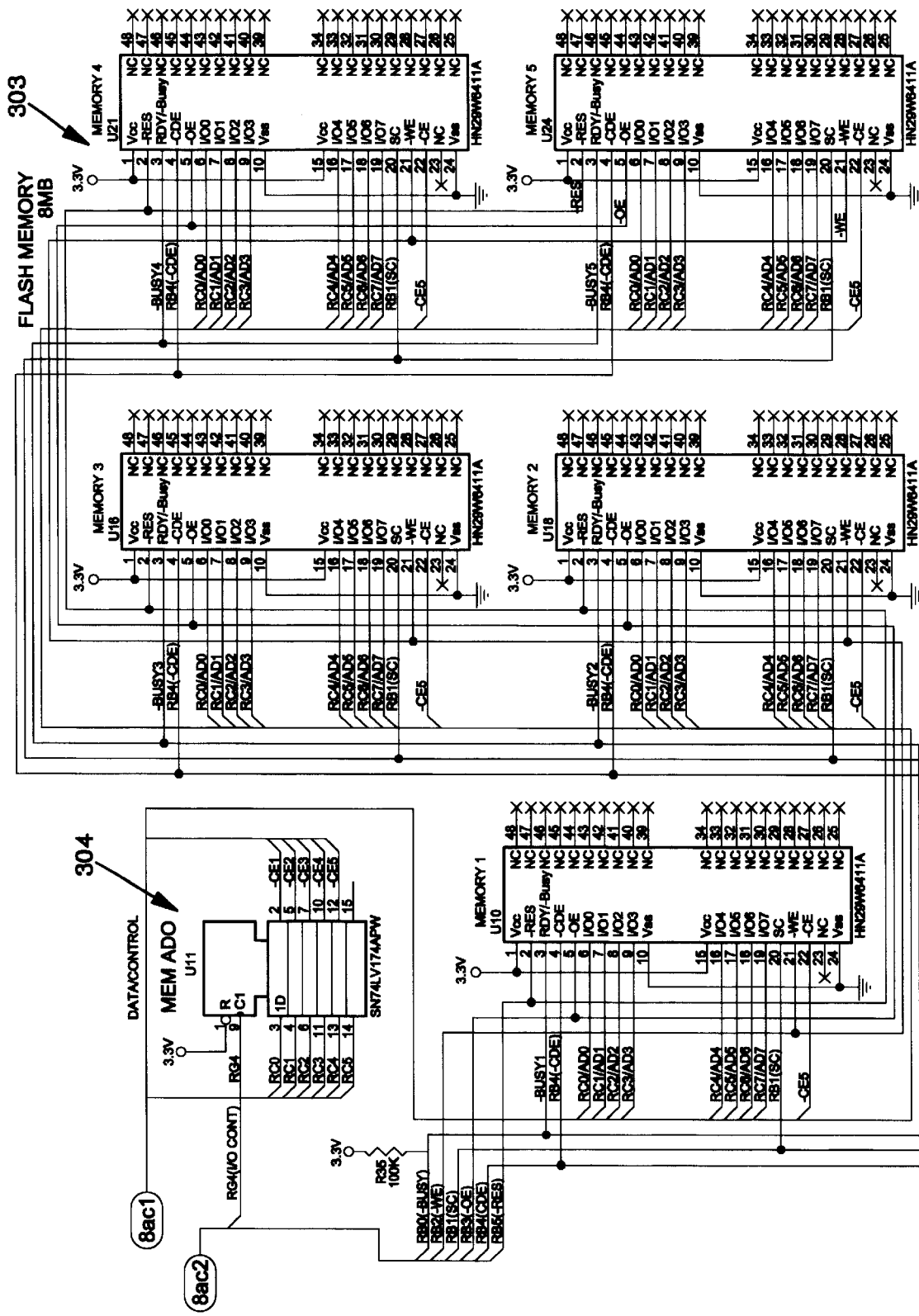

FIG. 8 delineates the system controller schematic. The data acquisition, storage and processing is accomplished and controlled by a microprocessor 300 on PCB 86 as regulated by a real time clock 301. Data is accumulated a bank of flash memory registers 302 through a memory address register 304. Upon completion of the monitoring period stored data is output through a universal serial buss (USB) with appropriate voltage conversion to output to a personal computer 308. LED driver circuits 310 are provided to give operator visual display of functions and operations of the controller circuit.

Figure 9:
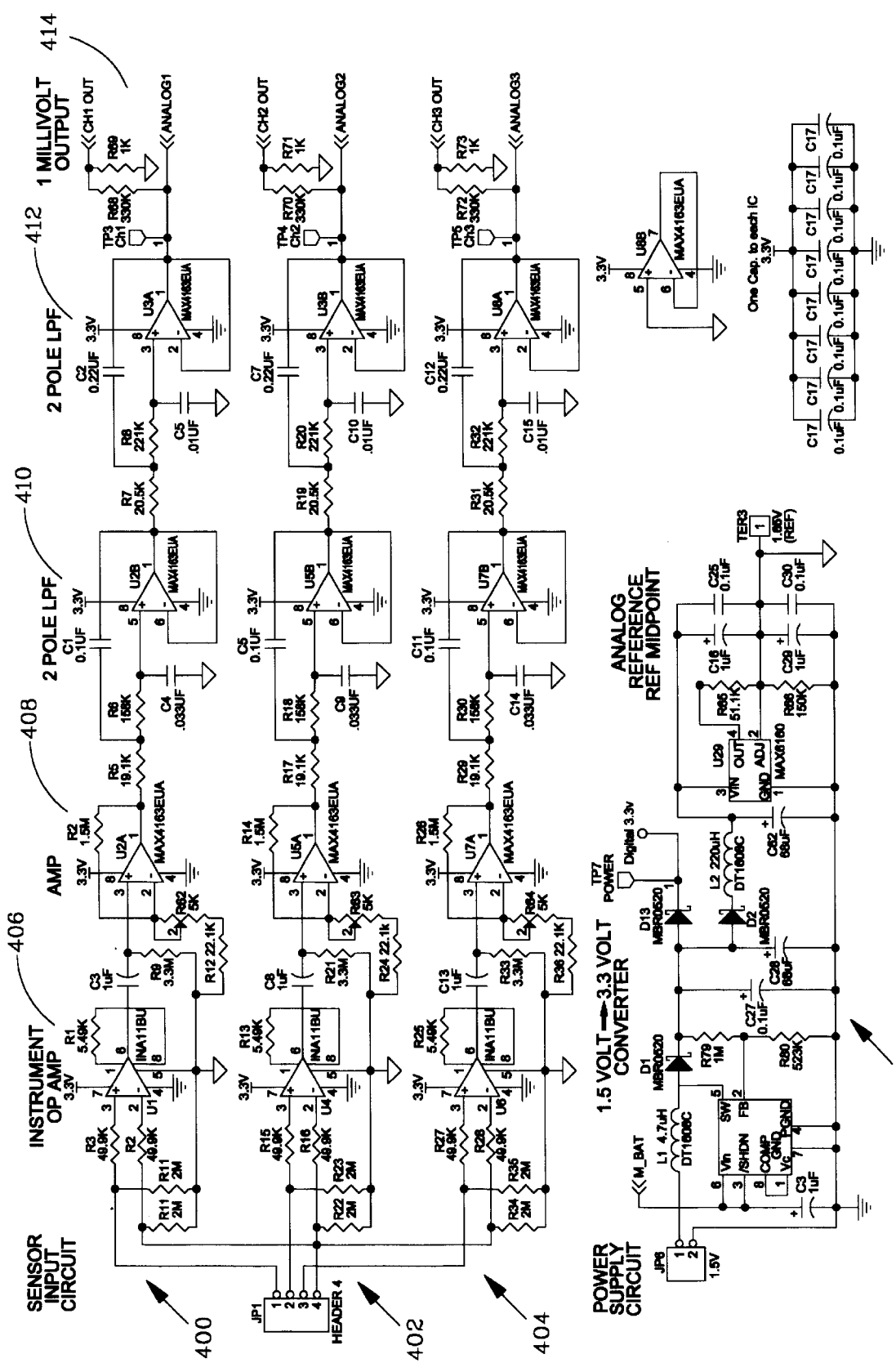
FIG. 9 depicts an electronic schematic of the physiological sensor analog input circuit and the system power supply circuit on the PCB.

FIG. 9 delineates the schematic for the three ECG electrode sensor circuits 400, 402 and 406. Data received for example by electrode, transducer 40 is first filtered through an op amp 406 and amplified by op amp 408 to be passed through a two pole low pass filter 410 and followed by a second two pole low pass filter 412 to yield an analog milivolt output 414. Second and third channels 402 and 404 operate in similar manner to yield three correlative channels of ECG and of course three cross sectional views of the heart. The power supply circuit 416 FIG. 9 indicates the method to convert the 1.5-volt battery source to the required 3.3 system voltage.

Figure 10:
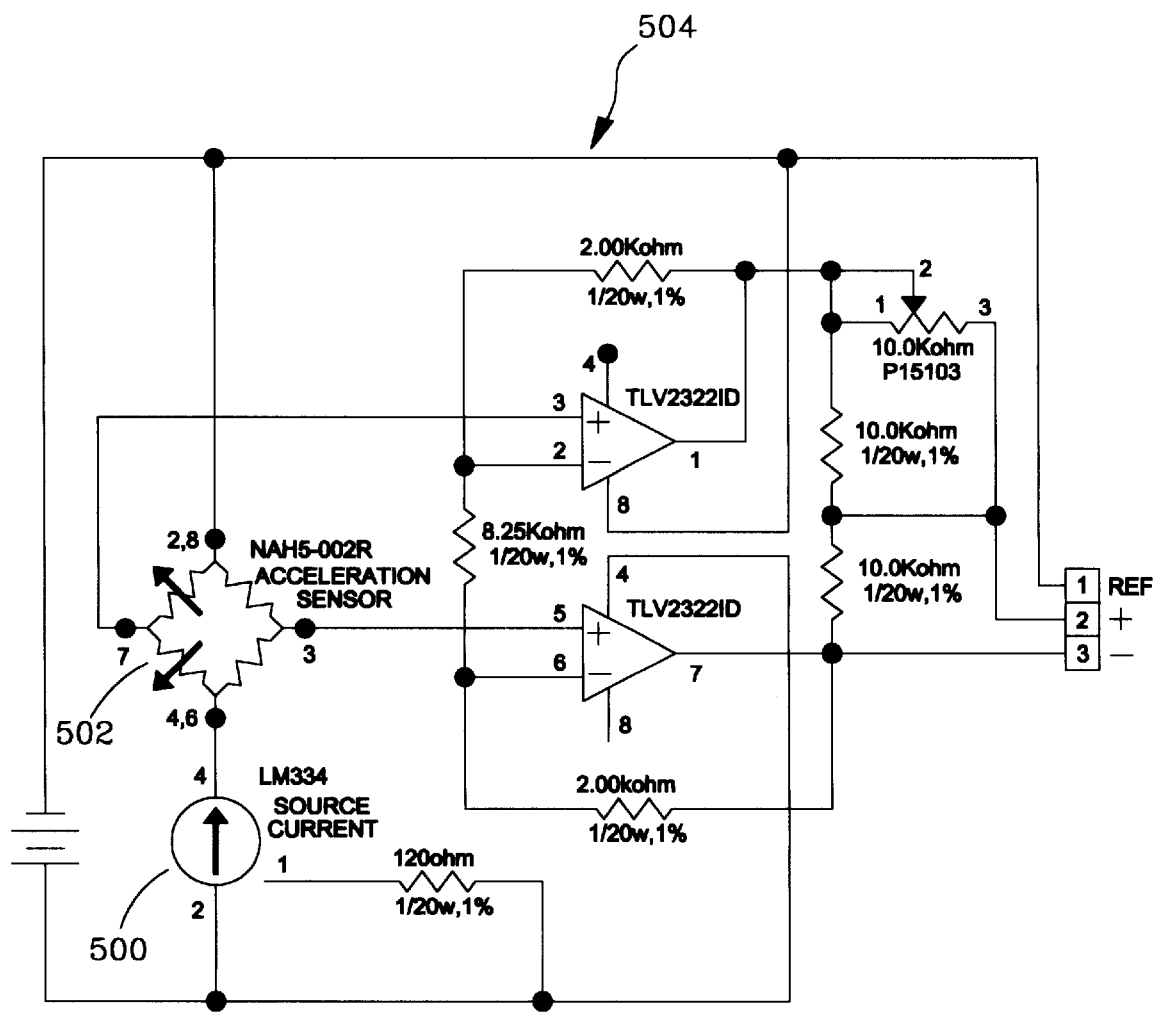
FIG. 10 depicts an electronic schematic of the acceleration sensor circuit on the PCB.

FIG. 10 delineates the accelerometer, activity monitor circuit. A piezoresistive accelerometer chip 500 is used to measure body movement. The output signal is conditioned in a balanced bridge 502 and produces a signal that is linearly proportional to acceleration. The activity monitor is calibrated to operate in the normal input signal range of Holter recorders. The signal conditioner circuit 504 is powered by the system 1.5 volt power supply converted to a 3 volt level in FIG. 9, and is configured to be running for a 24 hour period or more. The activity monitor system consists of the activity monitor sensor, i.e. accelerometer, the power supply/system battery, and an electrode adapter. The electrode adapter connects the output of the activity sensor module directly to the Holter recorder as channel 3. It is envisioned that activity readings will be summarized periodically at one-minute intervals.

Though the foregoing provides a somewhat detailed description of the invention disclosed, obvious embodiments, alterations and improvements are considered a part of the invention as well. The true scope and extent of the invention concept will be more clearly defined and delineated by the appended claims.

I claim:

1. An environmentally sealed, long term, ambulatory ECG data recorder and analyzer configured for mounting covertly under the clothing of a patient, comprising:

recorder housing;

environmentally protective envelope enclosing said housing;

at least one pivotal adhesive pad for mounting said envelope under a patient's clothing; and at least one active electrode transducer extending from said housing.

2. A long-term, ambulatory data recorder and data processor of physiological and kinetic data, comprising:

recorder housing having at least one active adhesive electrode for sensing physiological and kinetic data;

water repellant, environmental shield, envelope into which said recorder housing may be removably and securely inserted;

at least one inactive adhesive electrode for attaching said envelope, and recorder housing therein, covertly under a patient's clothing; and electrode pivot means disposed on said attaching electrode for permitting said attaching electrode to rotate about a point, and thereby permitting said envelope and housing disposed therein to likewise move about a point.

\* \* \* \* \*